United States Patent [19]

Evans et al.

[11] Patent Number: 4,988,498

[45] Date of Patent: Jan. 29, 1991

[54] ORAL COMPOSITIONS

[75] Inventors: Kenneth A. Evans, Chalfont St. Peter; Paul I. Biley; Brian Rossall, both of Bebington, all of Great Britain

[73] Assignee: Unilever Patent Holdings B.V., Rotterdam, Netherlands

[21] Appl. No.: 386,334

[22] Filed: Jul. 27, 1989

[51] Int. Cl.$^5$ .......................... A61K 7/16; A61K 7/18
[52] U.S. Cl. ...................................................... 424/52
[58] Field of Search .................................. 424/49, 52

[56] References Cited

U.S. PATENT DOCUMENTS

| | | | |
|---|---|---|---|
| 2,010,910 | 8/1935 | Atkins | 424/49 |
| 4,022,880 | 5/1977 | Vinson et al. | 424/49 |
| 4,100,269 | 7/1978 | Pader | 424/49 |
| 4,144,323 | 3/1979 | Lamberti | 424/54 |
| 4,160,821 | 7/1979 | Sipos | 424/145 |
| 4,168,301 | 9/1979 | Pugh et al. | 424/49 |
| 4,212,856 | 7/1980 | Hoyles | 424/49 |
| 4,529,584 | 7/1985 | Mulvey et al. | 424/49 |
| 4,529,585 | 7/1985 | Hayes | 424/49 |
| 4,656,031 | 4/1987 | Lane et al. | 424/49 |
| 4,781,982 | 11/1988 | Musselman et al. | 424/49 |

FOREIGN PATENT DOCUMENTS

| | | |
|---|---|---|
| 0251146 | 1/1988 | European Pat. Off. |
| 0304325 | 2/1989 | European Pat. Off. |
| 1277585 | 7/1972 | United Kingdom . |
| 1475252 | 6/1977 | United Kingdom . |
| 1537823 | 1/1979 | United Kingdom . |
| 2009596 | 6/1979 | United Kingdom . |
| 1544537 | 7/1979 | United Kingdom . |

OTHER PUBLICATIONS

Mordini et al., C.A. 99:55753x, (1983).
Evans et al., C.A. 112:83887z, (1990), EP 328406, Aug. 16, 1989.
Evans et al., C.A. 112:83888a, (1990) of EP 328407, Aug. 16, 1989.
"Effect of Seed and Temperature on the Particle Size of Bayer Hydrate", J. Scott in Extractive Metallurgy of Aluminium, vol. 1, (Interscience, New York), 1963, pp. 203-218.

*Primary Examiner*—Shep K. Rose
*Attorney, Agent, or Firm*—Milton L. Honig, Esq.

[57] ABSTRACT

The present invention relates to an oral composition such as a dentifrice. It has been found that the stability of a monofluorophosphate and a soluble zinc compound such as zinc citrate is improved in a dentifrice if instead of milled alumina trihydrate abrasive an unmilled precipitated alumina trihydrate abrasive is used in the dentifrice.

3 Claims, No Drawings

ORAL COMPOSITIONS

BACKGROUND OF THE INVENTION

1. Field of the Invention This invention relates to oral compositions, more particularly to oral compositions comprising as an abrasive cleaning agent particles of alumina trihydrate ($Al_2O_3 3H_2O$), sometimes referred to as aluminum trihydrate or aluminum hydroxide.

2. Description of the Related Art

Alumina trihydrate is a well-known abrasive agent of oral compositions such as toothpastes. It is made by the Bayer process which produces a coarse grade of material which is then milled to a particle size appropriate for use in an oral composition.

In GB No. 1 277 585 (Unilever) it is disclosed that toothpastes containing milled alumina trihydrate can cause corrosion of aluminum toothpaste tubes and that sodium monofluorophosphate and other sources of monofluorophosphate ions are effective to inhibit this corrosion. Certain phosphate esters are also disclosed as being effective in GB No. 1 475 252 (Colgate-Palmolive). The presence of certain materials during the milling process as disclosed in GB No. 1 537 823 (British Aluminum Co. Ltd) and GB No. 1 544 537 (Colgate-Palmolive) is said to modify the surface of the milled alumina trihydrate particles and make them more suitable for inclusion in toothpastes contained in aluminum tubes.

In GB No. 2 009 596 (Unilever) there is described a toothpaste containing MFP and alumina trihydrate abrasive but not containing zinc ion-producing compounds, wherein the abrasive consists of a mixture of an alumina trihydrate having an average particle size of from 5 to 13 microns and an alumina trihydrate having an average particle size of less than 1 micron, the weight ratio of the two alumina trihydrates being from 30:70 to 70:30. The sub-micron alumina trihydrate described has an average particle size of 0.2 to 0.8 micron, particularly about 0.5 micron. It is produced commercially as a fine precipitate and not by grinding larger particles.

It is nowadays common to include sodium monofluorophosphate in dentifrices as a source of fluoride to protect the teeth against dental caries.

We have determined that there is some interaction between sodium monofluorophosphate and an alumina trihydrate abrasive resulting in a loss of soluble fluoride on storage of a dentifrice, which is more marked at elevated temperatures. Thus, there may be some loss of anti-caries efficacy of such toothpastes.

SUMMARY OF THE INVENTION

It has now been discovered that the stability of monofluorophosphate in dentifrices containing an alumina trihydrate abrasive, and also containing a water-soluble zinc compound such as zinc citrate, is surprisingly improved if instead of employing a milled alumina trihydrate there is used an unmilled precipitated alumina trihydrate of appropriate particle size. The stability of soluble zinc in the dentifrice is also improved. Zinc citrate is a known anti-calculus and anti-plaque agent (see U.S. Pat. No. 4 100 269 (Pader).

DETAILED DESCRIPTION OF THE INVENTION

Accordingly, the invention relates to an oral composition comprising 20 to 70% by weight of an unmilled precipitated alumina trihydrate of average particle size 3 to 15 microns, preferably 5 to 10 microns, sodium monofluorophosphate in an amount of 0.1 to 2% by weight and a water-soluble zinc compound such as zinc citrate in an amount of 0.02 to 5% by weight.

The alumina abrasive used in oral compositions of this invention is made by a precipitation process which is a modification of that conventionally used to produce very fine alumina precipitates of average particle size 1-2 microns and below, in which process the precipitation conditions are varied so as to allow the growth of larger crystal aggregates. A suitable method to prepare the aluminas is described by J. Scott in a paper, "Effect of Seed and Temperature on the Particle Size of Bayer Hydrate", presented at the International Symposium on the Extractive Metallurgy of Aluminum, New York February 1962.

As indicated above, it has been found that the unmilled precipitated alumina abrasive has improved compatibility with soluble zinc compounds such as zinc citrate. Other suitable water-soluble zinc compounds which are well known for inclusion in oral compositions are disclosed in U.S. Pat. No. 4 100 269 (Pader) referred to above. Others are disclosed in U.S. Pat. No. 4 022 880 (Vinson et al.), U.S. Pat. No. 4 144 323 (Lamberti), U.S. Pat. No. 4 656 031 (Lane et al.) and U.S. Pat. No. 4 160 821 (Sipos). These references are herein incorporated by way of reference.

The amount of the zinc compound may be from about 0.02% to about 5% by weight of the oral composition.

Oral compositions of the invention will also contain other conventional ingredients. Those in the form of a dentifrice cream or gel will usually contain an humectant liquid, a surface-active agent, a binder or thickener and flavour. Other minor ingredients may also be present, such as up to 1% by weight of 2', 4, 4'-trichloro-2-hydroxy-diphenylether as antimicrobial agent.

The following experiments illustrate the invention. Percentages are by weight.

Toothpastes were made having the following composition.

| Ingredient | % |
| --- | --- |
| Alumina trihydrate | 50.0 |
| Sorbitol syrup (70% solution) | 27.0 |
| Sodium lauryl sulphate | 1.875 |
| Sodium dodecylbenzene sulphonate | 0.625 |
| Sodium carboxymethylcellulose | 0.8 |
| Zinc citrate trihydrate | 0.5 |
| Sodium monofluorophosphate | 0.85 |
| Flavour | 1.2 |
| Sodium saccharin | 0.2 |
| Formalin | 0.04 |
| Colour | 0.006 |
| Water to | 100.0 |

A number of toothpastes were formulated using the different grades of alumina trihydrate mentioned below:

1. Milled alumina trihydrate of average particle size 6-8 microns (available commercially from BA Chemicals as AF 280).
2. Milled alumina trihydrate of average particle size about 10 microns (available commercially from BA Chemicals as AF 240).
3. A precipitated (not milled alumina trihydrate of average particle size about 6 microns.

The respective toothpastes were stored at 37° C. for 6 months. The amount of water-soluble fluoride available after storage expressed as a percentage of that available immediately after manufacture is indicated in the Table below. The percentage of soluble zinc is also given in the Table.

| Abrasive present | % F | % Zn |
| --- | --- | --- |
| Milled alumina trihydrate, aps* 6–8 microns | 81 | 48 |
| Milled alumina trihydrate, aps about 10 microns | 92 | 37 |
| Precipitated alumina trihydrate, aps about 6 microns | 99 | 54 |

*average particle size

The results show the superior properties of the toothpastes according to this invention.

What is claimed is:

1. An oral composition consisting essentially of 0.1–2% by weight of sodium monofluorophosphate, 0.02–5% by weight of a water-soluble zinc compound and from 20–70% by weight of an unmilled precipitated alumina trihydrate with an average particle size of between 3 and 15 microns.

2. A composition according to claim 1, wherein the zinc compound is zinc citrate.

3. A composition according to claim 1, wherein the alumina trihydrate has an average particle size of between 5 and 10 microns.

* * * * *

UNITED STATES PATENT AND TRADEMARK OFFICE
CERTIFICATE OF CORRECTION

PATENT NO. : 4,988,498
DATED : January 29, 1991
INVENTOR(S) : Evans et al.

It is certified that error appears in the above-indentified patent and that said Letters Patent is hereby corrected as shown below:

On the title page: Item [75] Inventors:

"Paul I. Biley" should read -- Paul I. Riley --.

Signed and Sealed this

Third Day of May, 1994

*Attest:*

BRUCE LEHMAN

*Attesting Officer*     Commissioner of Patents and Trademarks